(12) United States Patent
Xiao et al.

(10) Patent No.: US 11,219,727 B2
(45) Date of Patent: Jan. 11, 2022

(54) MEDICAL SUPPORTABLE VARIABLE TRACHEAL TUBE VENTILATION DEVICE

(71) Applicant: Jinfang Xiao, Guangdong (CN)

(72) Inventors: Jinfang Xiao, Guangdong (CN); Ming Xiao, Guangdong (CN)

( * ) Notice: Subject to any disclaimer, the term of this patent is extended or adjusted under 35 U.S.C. 154(b) by 568 days.

(21) Appl. No.: 16/099,441

(22) PCT Filed: Jun. 13, 2017

(86) PCT No.: PCT/CN2017/088123
§ 371 (c)(1),
(2) Date: Nov. 7, 2018

(87) PCT Pub. No.: WO2018/223409
PCT Pub. Date: Dec. 13, 2018

(65) Prior Publication Data
US 2021/0220589 A1     Jul. 22, 2021

(51) Int. Cl.
*A61M 16/04* (2006.01)
*A61M 16/20* (2006.01)

(52) U.S. Cl.
CPC ...... *A61M 16/045* (2014.02); *A61M 16/0418* (2014.02); *A61M 16/0463* (2013.01); *A61M 16/0475* (2014.02); *A61M 16/20* (2013.01); *A61M 2205/0216* (2013.01); *A61M 2205/0266* (2013.01)

(58) Field of Classification Search
CPC .......... A61M 16/0418; A61M 16/0463; A61M 16/0475; A61M 16/0875; A61M 16/20
See application file for complete search history.

(56) References Cited

U.S. PATENT DOCUMENTS

| | | | | |
|---|---|---|---|---|
| 3,169,529 A | * | 2/1965 | Koenig | A61M 16/0427 128/207.14 |
| 3,409,224 A | * | 11/1968 | Harp | A47G 21/186 239/33 |
| 3,538,918 A | * | 11/1970 | Hofstra | A61M 16/0427 128/200.26 |
| 3,788,326 A | * | 1/1974 | Jacobs | A61M 16/16 128/207.15 |
| 3,880,168 A | * | 4/1975 | Berman | A61M 16/0445 128/207.15 |
| 4,050,466 A | * | 9/1977 | Koerbacher | A61M 16/04 128/207.14 |

(Continued)

*Primary Examiner* — Kathryn E Ditmer (57) ABSTRACT

A medical supportable variable tracheal tube ventilation device, having a tracheal tube main body having a telescopic length; the tracheal tube main body comprises a telescopic tracheal tube main tube achieved by compressible sections and a variable tracheal tube head coupled to one end of the tracheal tube main tube; the tracheal tube head is made of a material shapable according to different temperatures; the variable tracheal tube head is a compressed cone, and by airflow inflation, the compressed cone of the variable tracheal tube head expands and opens to the cylindrical shape; an outer side of the tracheal tube main body is sleeved with a tracheal tube sealing cuff, and the tracheal tube sealing cuff is disposed proximal to the variable tracheal tube head; another end of the tracheal tube main tube is connected with a tracheal tube connector.

13 Claims, 5 Drawing Sheets

(56) References Cited

U.S. PATENT DOCUMENTS

| | | | | | |
|---|---|---|---|---|---|
| 4,141,364 | A | * | 2/1979 | Schultze | A61M 16/04 128/207.15 |
| 4,211,234 | A | * | 7/1980 | Fisher | A61M 16/0488 128/200.26 |
| 4,275,724 | A | * | 6/1981 | Behrstock | A61M 16/0463 128/207.14 |
| 4,340,089 | A | * | 7/1982 | Freiherr von Arnim | F16J 3/047 138/121 |
| 4,417,874 | A | * | 11/1983 | Andersson | A61C 17/08 433/96 |
| 4,852,564 | A | * | 8/1989 | Sheridan | A61M 16/04 128/202.27 |
| 4,987,895 | A | * | 1/1991 | Heimlich | A61M 16/0465 128/207.14 |
| 5,447,503 | A | * | 9/1995 | Miller | A61M 25/0068 604/528 |
| 5,537,729 | A | * | 7/1996 | Kolobow | A61M 16/04 29/527.2 |
| 5,743,258 | A | * | 4/1998 | Sato | A61M 16/0456 128/207.15 |
| 5,762,638 | A | * | 6/1998 | Shikani | A61K 9/0024 604/265 |
| 6,148,818 | A | * | 11/2000 | Pagan | A61M 16/04 128/207.15 |
| 6,358,238 | B1 | * | 3/2002 | Sherry | A61M 25/0023 604/524 |
| 6,761,703 | B2 | * | 7/2004 | Miller | A61M 25/0074 604/96.01 |
| 7,607,634 | B2 | * | 10/2009 | Browne | F16K 7/02 138/46 |
| 8,651,142 | B2 | * | 2/2014 | Sellers | F03G 7/065 138/45 |
| 2002/0195110 | A1 | * | 12/2002 | Watton | A61M 16/04 128/207.15 |
| 2008/0078406 | A1 | * | 4/2008 | Clayton | A61M 16/04 128/207.15 |
| 2009/0156953 | A1 | * | 6/2009 | Wondka | A61B 5/085 600/538 |
| 2009/0211572 | A1 | * | 8/2009 | Matera | A61M 16/0459 128/200.26 |
| 2009/0248141 | A1 | * | 10/2009 | Shandas | A61B 17/12159 623/1.19 |
| 2011/0073115 | A1 | * | 3/2011 | Wood | A61M 16/0436 128/207.15 |
| 2011/0197895 | A1 | * | 8/2011 | Stephenson | A61M 16/0816 128/207.14 |
| 2012/0180796 | A1 | * | 7/2012 | Bateman | A61M 16/0465 128/207.14 |
| 2012/0323180 | A1 | * | 12/2012 | Chebator | A61M 25/0668 604/164.03 |
| 2014/0196724 | A1 | * | 7/2014 | Morris | A61M 16/0472 128/207.29 |
| 2015/0090270 | A1 | * | 4/2015 | Bowers | A61M 16/0445 128/207.15 |
| 2015/0151094 | A1 | * | 6/2015 | Lewer | A61M 16/0461 606/196 |
| 2017/0095629 | A1 | * | 4/2017 | Bateman | A61M 16/0465 |
| 2017/0312112 | A1 | * | 11/2017 | Gobel | A61F 5/0043 |
| 2018/0193580 | A1 | * | 7/2018 | Dem rc | A61M 16/0479 |

* cited by examiner

MEDICAL SUPPORTABLE VARIABLE TRACHEAL TUBE VENTILATION DEVICE

BACKGROUND OF THE INVENTION

The present invention relates to the technical field of medical equipment, and more specifically relates to a medical supportable variable tracheal tube ventilation device.

Tracheal intubation refers to the technique of placing a specific tracheal tube through the glottis into the trachea. This technique can provide optimal conditions for tracheal patency, oxygen ventilation, respiratory attraction and prevention of aspiration.

The tracheal tube in the prior art mainly comprises: a tracheal tube main body, an air outlet at one end of the tracheal tube main body, and an air inlet connectable with an oxygen tube at another end of the tracheal tube main body. During use, the tracheal tube main body is inserted into the upper respiratory tract of a patient through the glottis, and then being fixed, and the air inlet is connected to a ventilation device for assisted breathing of the patient, thereby satisfying the patient's demand for oxygen.

However, the inventors of the present invention discover that the tracheal tube according to the prior art is more irritative to the airway of a patient, who may find such irritation hard to bear, especially tracheal tube induced bucking and coughing reflexes experienced when the patient recovers from general anesthesia. Bucking and coughing reflexes can cause unstable circulatory dynamics, severe fluctuations in blood pressure, respiratory depression, increased abdominal pressure, all being the causes of bleeding and cracked wounds. Also, a long period of time inserted with the tracheal tube leads to airway infection.

Specifically, connection of an intraoperative ventilation device and an anesthesia device to a patient subject to perioperative general anesthesia is mainly achieved by a traditional tracheal tube or a laryngeal mask. Use of the laryngeal mask is an important means to relieve the hypersensitive reaction of the airway of the patient who is under general anesthesia, but there are also limitations to the use of the laryngeal mask, for example, it can only be used in surgeries that last for about 4 hours, patients found to have air leakage and with special postures are not suitable to use the laryngeal mask, and brain surgery patients are not suitable to use the laryngeal mask. Also, a long period of use of the laryngeal mask can be accompanied by oropharyngeal pain, hoarseness, and wheezing. Traditional tracheal tubes are still commonly used, but serious bucking and coughing reflexes will be induced by irritation of the tracheal tube when the patient recovers from general anesthesia. In recent years, attention is given to some methods dedicated to prevent brain injury caused by postoperative bucking and coughing responses induced by tracheal tube after brain surgery. Propofol can relieve bucking and coughing, but like all other drugs, drug metabolism increases workload of the liver; the use of opioid analgesics can effectively relieve pain, reduce bucking and coughing reflexes, but may increase the chances of postoperative nausea, vomiting and respiratory depression. Dexmedetomidine can improve a patient's tolerance against the tracheal tube during recovery from general anesthesia, but drug metabolism increases the body workload and also affects circulatory function; the above anesthetic drugs are disadvantageous to the recovery of postoperative consciousness, and thus delay the patient's recovery. During recovery from general anesthesia in perioperative period wherein respiratory and swallowing reflexes are recovered, phlegm suction and extubation cause the tracheal mucosa to be directly stimulated by the tracheal tube, thereby possibly casing serious bucking and coughing reflexes which lead to severe fluctuation of hemodynamics that increases the concentrations of plasma adrenaline and norepinephrine, increases peripheral vascular resistance, and increases pulmonary vascular resistance, of which the clinical manifestations are shortness of breath, increased heart rate, and a surge of blood pressure; and the resulting imbalance of myocardial oxygen supply and oxygen consumption can also cause complications such as myocardial ischemia, heart failure and arrhythmia; especially, cardiovascular accidents can be induced in patients with a history of hypertension or diabetes; moreover, bucking and coughing may create wounds and causes bleeding and cracking of wounds. Therefore, a series of complications caused by tracheal tube induced bucking and coughing reflexes during recovery from general anesthesia represent the focus of and also the difficulty in perioperative airway management and are receiving more and more attention. Bucking and coughing are characterized by a huge intra-thoracic pressure and a strong airflow. The intra-thoracic pressure can be transmitted to a wound surface through blood vessels, and thus causing the wound surface to bleed. Clinically, there are many drugs for preventing bucking and coughing or reducing the stress response to the tracheal tube, such as opioid analgesics, propofol, and dexmedetomidine, etc.; anesthetics can alleviate bucking and coughing, but delay the patient's recovery and the quality of recovery, and also increase the workload on liver and kidney for drug metabolism.

Taking cranial tumor surgery as an example, patients will experience bucking and coughing responses during recovery from anesthesia or during phlegm suction, and most of the bucking and coughing responses occur during removal of the tracheal tube. Bucking and coughing can cause wounds on the brain to bleed, and can cause brain swelling, cerebral hematoma, and elevated intracranial pressure, susceptible of causing secondary brain injury (SBI). In clinical anesthesia, the airway response induced by the tracheal tube on the body during recovery from general anesthesia is obvious, namely, serious bucking and coughing reactions are resulted, which lead to elevated concentration of plasma adrenaline and norepinephrine, increased peripheral vascular resistance, and increased pulmonary vascular resistance. The instability of breathing and circulatory system is characterized by shortness of breath, increased heart rate, and a surge in blood pressure; the resulting imbalance of myocardial oxygen supply and oxygen consumption can also cause myocardial ischemia, which can affect organ perfusion and tissue oxygenation, and can be seriously harmful to patients with complications like hypertension or diabetes or patients with heart diseases due to resulting complications like severe myocardial ischemia, heart failure and arrhythmia. Therefore, researches on airway management during cranial surgery as well as a series of pathophysiological reactions such as bucking and coughing induced by tracheal tube after recovery are received with more and more attention.

In In clinical anesthesia of patients undergoing liver surgery, the airway response induced by the tracheal tube on the body during recovery from general anesthesia is obvious, namely, serious bucking and coughing reactions are resulted, which may also easily cause bleeding of wounds. Patients also with hypertension, diabetes, obesity and snoring are also susceptible to associated complications.

Therefore, the technical question desperately requiring a solution from a skilled person in the field of art is how to provide a safer medical supportable variable tracheal tube ventilation device which can minimize irritation to the airway caused by the tracheal tube during perioperative general anesthesia and which can effectively improve the patient's tolerance.

BRIEF SUMMARY OF THE INVENTION

The object of the present invention is to provide a medical supportable variable tracheal tube ventilation device, which solves the existing technical problem of greater tracheal tube induced airway irritation which patients may consider hard to bear.

A medical supportable variable tracheal tube ventilation device, comprising a tracheal tube main body having a telescopic length; the tracheal tube main body comprises a telescopic tracheal tube main tube achieved by compressible sections and a variable tracheal tube head coupled to one end of the tracheal tube main tube; the tracheal tube head is made of a material shapable according to different temperatures: when the temperature is above 30 degrees Celsius or 86 degrees Fahrenheit, the variable tracheal tube head opens to form a cylindrical shape; when the temperature is below 10 degrees Celsius or 18.6 degrees Fahrenheit, the variable tracheal tube head returns to a tapered shape; the variable tracheal tube head is a compressed cone, and by airflow inflation, the compressed cone of the variable tracheal tube head expands and opens to the cylindrical shape; an outer side of the tracheal tube main body is sleeved with a tracheal tube sealing cuff, and the tracheal tube sealing cuff is disposed proximal to the variable tracheal tube head; another end of the tracheal tube main tube is connected with a tracheal tube connector.

Specifically, when the variable tracheal tube head is in the cylindrical shape for ventilation, a diameter of the variable tracheal tube head is equal to a diameter of the tracheal tube main tube.

Further, the variable tracheal tube head is provided with side openings.

Optionally, a quantity of the side openings is at least two.

Optionally, the side openings are distributed to form a triangular shape within a three-dimensional space.

Optionally, the side openings are distributed in a cross shape within a three-dimensional space.

Optionally, the side openings are distributed in a rectangular shape within a three-dimensional space.

In actual applications, the tracheal tube main tube is mainly made of antibacterial PVC elastic film or antibacterial paper material elastic film; a thickness of the PVC elastic film or paper material elastic film is from 0.07 mm to 0.17 mm.

The telescopic tracheal tube main tube achievable by compressible sections has an extended length of at least twice a length of the same when all sections are compressed; when the telescopic tracheal tube main tube is inserted from the oral cavity into the trachea, the sections at a distal end of the tracheal tube are first being extended; when the telescopic tracheal tube main tube is retrieved back from the trachea to the oral cavity, the sections at a proximal end of the tracheal tube are first being compressed; each of the sections has a thickness of less than 1.3 mm.

Specifically, a guiding tube is provided inside the tracheal tube main tube; rail holes are provided on the guiding tube along an axial direction of the guiding tube; elastic support members are provided sequentially with spaced intervals in the tracheal tube main tube along an axial direction of the tracheal tube main tube; the elastic support members provide circumferential support of the tracheal tube main tube; a diameter of each of the elastic support members is 0.1 mm to 0.2 mm; the guiding tube is disposed through eyelets of the elastic support members, and the tracheal tube main body telescopically slides on the guide tube.

Further, the guiding tube participates in ventilation, and each of the rail holes on a wall of the guiding tube has a tear drop shape and participates in ventilation.

Further, a diameter of a head portion of each of the tear drop shaped rail holes on the guiding tube is 1 mm, and a diameter of a tail portion thereof is 0.1-0.2 mm.

Preferably, each of the elastic support members is a spring.

In actual applications, the tracheal tube sealing cuff is connected with an inflation valve.

Compared with the prior art, the medical supportable variable tracheal tube ventilation device according to an embodiment of the present invention has the following advantages:

The medical supportable variable tracheal tube ventilation device provided by the present invention comprises a tracheal tube main body having a telescopic length; the tracheal tube main body comprises a telescopic tracheal tube main tube achieved by compressible sections and a variable tracheal tube head coupled to one end of the tracheal tube main tube; the tracheal tube head is made of a material shapable according to different temperatures: when the temperature is above 30 degrees Celsius or 86 degrees Fahrenheit, the variable tracheal tube head opens to form a cylindrical shape; when the temperature is below 10 degrees Celsius or 50 degrees Fahrenheit, the variable tracheal tube head returns to a tapered shape. The variable tracheal tube head may be a compressed cone, and by airflow inflation, the compressed cone of the variable tracheal tube head can expand and open to a cylindrical shape. An outer side of the tracheal tube main body is sleeved with a tracheal tube sealing cuff, and the tracheal tube sealing cuff is disposed proximal to the variable tracheal tube head; another end of the tracheal tube main tube is connected with a tracheal tube connector. As shown and described, it can be understood that the medical supportable variable tracheal tube ventilation device provided by an embodiment of the present invention allows the shape of the variable tracheal tube head to be changed for ventilation, and the length of the tracheal tube main body can also be changed according to the telescopic tracheal tube main tube, therefore, the medical supportable variable tracheal tube ventilation device provided by the present invention can minimize tracheal tube induced irritation to the airway during perioperative general anesthesia, and effectively increases patient's tolerance, and is also safer. In addition, the patient can make a conversation when awake even with the tracheal tube, and recovery of the patient or re-insertion of the tracheal tube to the patient can be achieved at any time in case of emergency. The present invention is therefore especially suitable for a patient who needs to use the tracheal tube when being transferred back to the ward or ICU.

BRIEF DESCRIPTION OF THE DRAWINGS

In order to illustrate more clearly the technical solution of the prior arts and of the embodiments of the medical supportable variable tracheal tube ventilation device according to an embodiment of the present invention, the drawings necessary to illustrate the embodiments and the prior arts are briefly described below. Obviously, the drawings as described only illustrate some specific embodiments of the present invention. Other drawings obtainable without any inventive effort by a person skilled in this field of art based on the teachings of the drawings herein should also fall within the scope of protection of the present invention.

References in the drawings.

1—tracheal tube main body; 11—telescopic tracheal tube main tube; 12—variable tracheal tube head; 2—tracheal tube sealing cuff; 3—tracheal tube connector 3; 121—side openings; 4—guiding tube; 41—rail holes; 5—elastic support members; 55—eyelets of the elastic support members; 6—inflation valve.

DETAILED DESCRIPTION OF THE INVENTION

The present invention will be clearly and comprehensively described below with reference to the drawings. Obviously, the embodiments described as follows are only part but not all of the embodiments of the present invention. All other embodiments obtainable without any inventive effort by a person skilled in this field of art based on the teachings of the embodiments of the present invention should fall within the scope of protection of the present invention.

It should be noted that, in the following description, terms like "center", "upper", "lower", "left", "right", "vertical", "horizontal", "inside" and "outside" that indicate directions or positional relationships should be understood according to the directions or positional relationships as shown in the drawings, and they are intended only for convenient and simplified description of the present invention, and should not be understood to bear any indication or implication of limiting the device or components as described to be necessarily being oriented, structured and operated according to the specifically described directions, and so they should not limit the present invention. Also, terms like "first", "second" and third" are intended only for illustration and have no indication or implication regarding the relative importance of the elements being described.

It should be noted that, in the following description of the present invention, terms like "installed", "connected", "communicated" should be interpreted broadly, unless otherwise specified and limited. For example, connection can be interpreted as fixed connection, removable connection or connection as a one whole piece, and it can be achieved mechanically as well as electrically, directly or indirectly through a medium, or it may refer to internal connection of two components. A person skilled in this field of art may interpret the specific meaning of the terms in a specific occurrence in the following description according to the specific context of the description.

Figure 1:
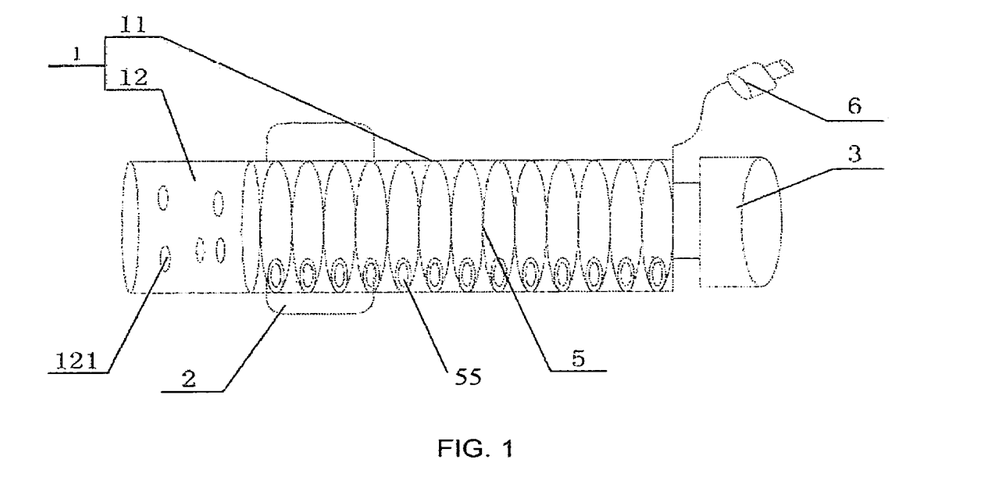
FIG. 1 is a structural view of the medical supportable variable tracheal tube ventilation device according to an embodiment of the present invention in a first operating state.
Figure 2:
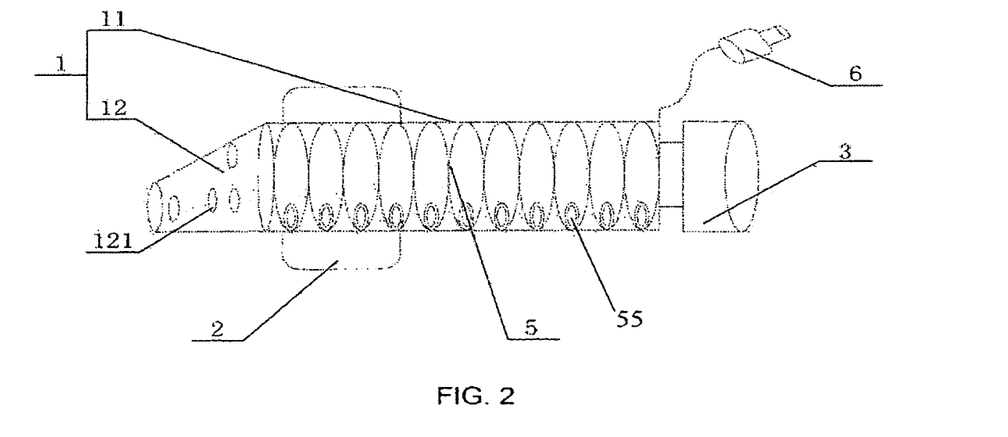
FIG. 2 is a structural view of the medical supportable variable tracheal tube ventilation device according to an embodiment of the present invention in a second operating state.

FIG. 1 is a structural view of the medical supportable variable tracheal tube ventilation device according to an embodiment of the present invention in a first operating state. FIG. 2 is a structural view of the medical supportable variable tracheal tube ventilation device according to an embodiment of the present invention in a second operating state.

As shown in FIGS. 1 and 2, the medical supportable variable tracheal tube ventilation device according to an embodiment of the present invention comprises a tracheal tube main body 1 having a telescopic length; the tracheal tube main body 1 comprises a telescopic tracheal tube main tube 11 achieved by compressible sections and a variable tracheal tube head 12 coupled to one end of the tracheal tube main tube 11; the tracheal tube head 12 is made of a material shapable according to different temperatures: when the temperature is above 30 degrees Celsius or 86 degrees Fahrenheit, the variable tracheal tube head 12 opens to form a cylindrical shape; when the temperature is below 10 degrees Celsius or 50 degrees Fahrenheit, the variable tracheal tube head 12 returns to a tapered shape. The variable tracheal tube head 12 may be a compressed cone, and by airflow inflation, the compressed cone of the variable tracheal tube head 12 can expand and open to a cylindrical shape. An outer side of the tracheal tube main body 1 is sleeved with a tracheal tube sealing cuff 2, and the tracheal tube sealing cuff 2 is disposed proximal to the variable tracheal tube head 12; another end of the tracheal tube main tube 11 is connected with a tracheal tube connector 3.

Compared with the prior art, the medical supportable variable tracheal tube ventilation device according to an embodiment of the present invention has the following advantages:

The medical supportable variable tracheal tube ventilation device provided by the embodiment of the present invention, as shown in FIG. 1 and FIG. 2, comprises: a tracheal tube main body 1 having a telescopic length; the tracheal tube main body 1 comprises a telescopic tracheal tube main tube 11 achieved by compressible sections and a variable tracheal tube head 12 coupled to one end of the tracheal tube main tube 11; the tracheal tube head 12 is made of a material shapable according to different temperatures: when the temperature is above 30 degrees Celsius or 86 degrees Fahrenheit, the variable tracheal tube head 12 opens to form a cylindrical shape; when the temperature is below 10 degrees Celsius or 50 degrees Fahrenheit, the variable tracheal tube head 12 returns to a tapered shape. The variable tracheal tube head 12 may be a compressed cone, and by airflow inflation, the compressed cone of the variable tracheal tube head 12 can expand and open to a cylindrical shape. An outer side of the tracheal tube main body 1 is sleeved with a tracheal tube sealing cuff 2, and the tracheal tube sealing cuff 2 is disposed proximal to the variable tracheal tube head 12; another end of the tracheal tube main tube 11 is connected with a tracheal tube connector 3. As shown and described above, it can be understood that the medical supportable variable tracheal tube ventilation device provided by an embodiment of the present invention allows the shape of the variable tracheal tube head 12 to be changed for ventilation, and the length of the tracheal tube main body 1 can also be changed according to the telescopic tracheal tube main tube 11, therefore, the medical supportable variable tracheal tube ventilation device provided by an embodiment of the present invention can minimize tracheal tube induced irritation to the airway during perioperative general anesthesia, and effectively increases patient's tolerance, and is also safer. In addition, the patient can make a conversation when awake even with the tracheal tube, and recovery of the patient or re-insertion of the tracheal tube to the patient can be achieved at any time in case of emergency. The present invention is therefore especially suitable for a patient who needs to use the tracheal tube when being transferred back to the ward or ICU.

In the medical supportable variable tracheal tube ventilation device provided by an embodiment of the present invention, the variable tracheal tube head 12 can switch between a truncated cone shaped ventilation state (as shown in FIG. 2) and a cylindrical ventilation state (as shown in the FIG. 1).

Specifically, as shown in FIG. 1, when the variable tracheal tube head 12 is in a cylindrical ventilation state, a diameter of the variable tracheal tube head 12 is equal to a diameter of the tracheal tube main tube 11.

Further, as shown in FIG. 1 and FIG. 2, in the medical supportable variable tracheal tube ventilation device provided by an embodiment of the present invention, the variable tracheal tube head 12 is provided with side openings 121; the side opening 121 can effectively improve ventilation effect.

Further, as shown in FIG. 1 and FIG. 2, in the medical supportable variable tracheal tube ventilation device provided by an embodiment of the present invention, a quantity of the side openings 121 is at least two; a plurality of side openings 121 can render the ventilated airflow more similar to the mixed flow in physiology, improve convergence of the ventilated airflow, and ensure that the ventilated airflow can be more concentrated.

Optionally, when the quantity of the side openings 121 is three, the three side openings 121 may be distributed to form a triangular shape within a three-dimensional space, and the triangular shape as formed may be an isosceles triangle, that is, a triangle with two of the three included angles being equal; or, the triangular shape as formed may be an equilateral triangle, that is, a triangle with all the three included angles being 60 degrees; or the triangular shape as formed may be a right angled triangle, that is, a triangle having an included angle of 90 degrees among the three included angles; or the triangular shape as formed may be an right angled isosceles triangle, that is, a triangle having an included angle of 90 degrees and the other two included angles being 45 degrees respectively; or the triangular shape as formed may be a right angled triangle with one included angle being 30 degrees, that is, a triangle with the first included angle being 30 degrees, a second included angle being 60 degrees, and a third included angle being 90 degrees.

Of course, besides the specific triangles listed above, the triangular shape as formed may also be a triangle having included angles with any suitable degrees of angles. Although not being specifically described herein, all other possible triangles should also fall within the scope of protection of the present invention.

Optionally, when there are four side openings 121, the four side openings 121 may be distributed in a cross shape within the three-dimensional space, and the width and height of the cross are equal; of course, the cross may have unequal width and height.

Optionally, when there are four side openings 121, the four side openings 121 may be distributed in a rectangular shape within the three-dimensional space. For example, the four side openings 121 form a parallelogram within the three-dimensional space.

In practical applications, in order to reduce the possibility of incision on the trachea, in the medical supportable variable tracheal tube ventilation device provided by an embodiment of the present invention, the tracheal tube main tube 11 is mainly made of metal and non-metal nano antibacterial materials featuring antibacterial properties, and preferably being an antibacterial PVC elastic film. By adopting the antibacterial properties of the nano antibacterial materials and because of the advantages of the structure of the tracheal tube, the present invention can be used in ICU, and can extend the intubated time period for patients requiring respiratory muscle support, thereby effectively reducing the possibility of incision on the trachea.

Of course, the tracheal tube main tube 11 can also be made of other films that satisfy the requirements, for example, an antibacterial paper material elastic film. Further, the thickness of the above PVC material or paper material can be from 0.07 mm to 0.17 mm.

Figure 3:
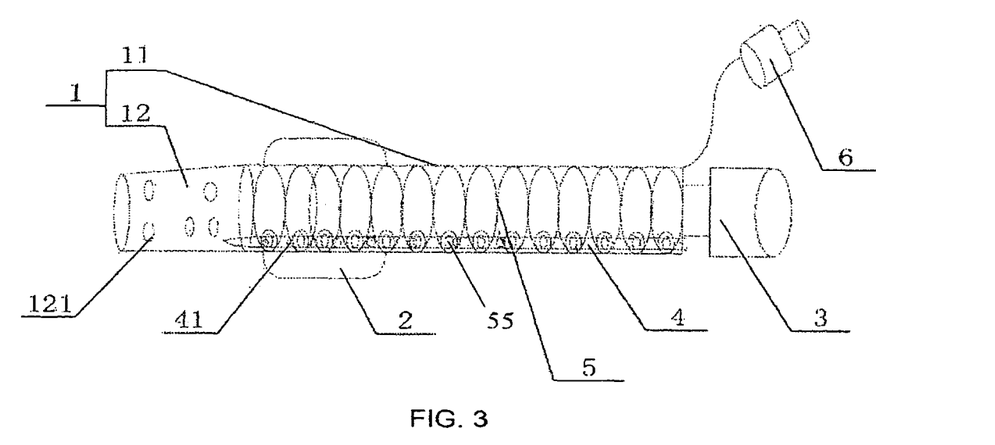
FIG. 3 is a structural view of a medical supportable variable tracheal tube ventilation device according to another embodiment of the present invention.
Figure 4:
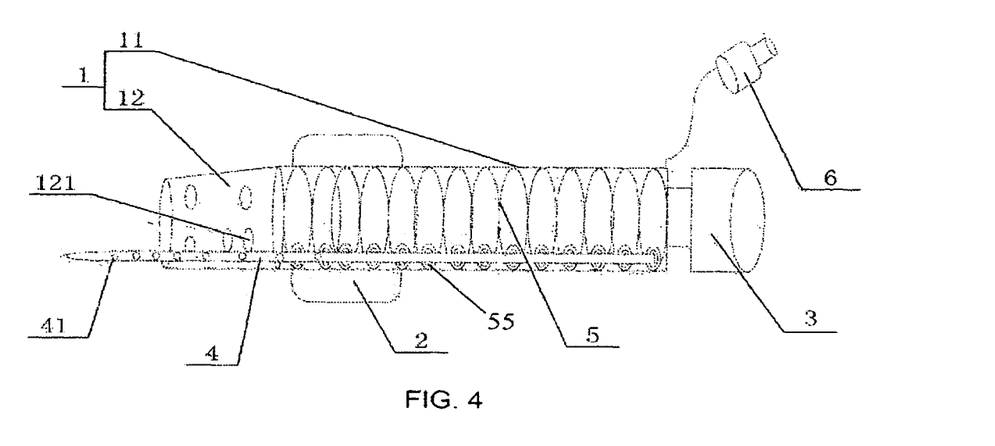
FIG. 4 is a structural view of the medical supportable variable tracheal tube ventilation device according to the other embodiment of the present invention in a first telescopic length.
Figure 5:
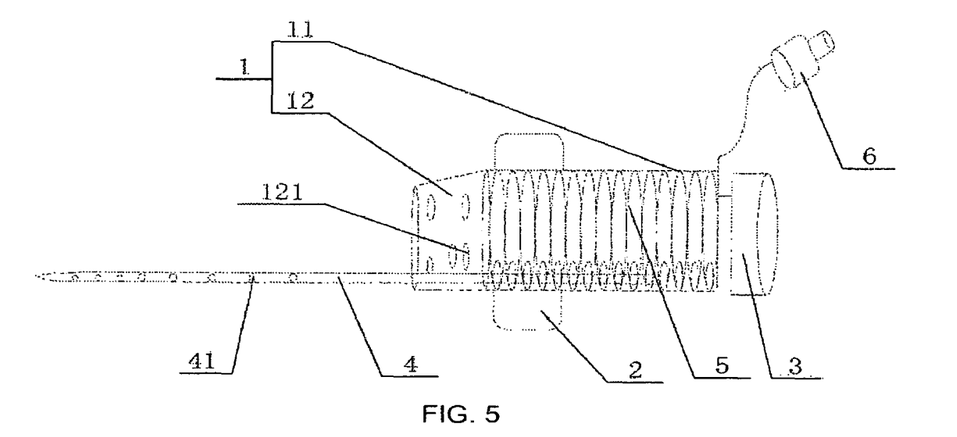
FIG. 5 is a structural view of the medical supportable variable tracheal tube ventilation device according to the other embodiment of the present invention in a second telescopic length.

FIG. 3 is a structural view of a medical supportable variable tracheal tube ventilation device according to another embodiment of the present invention; FIG. 4 is a structural view of the medical supportable variable tracheal tube ventilation device according to the other embodiment of the present invention in a first telescopic length; FIG. 5 is a structural view of the medical supportable variable tracheal tube ventilation device according to the other embodiment of the present invention in a second telescopic length.

As shown in FIG. 3 to FIG. 5, in the medical supportable variable tracheal tube ventilation device provided by an embodiment of the present invention, the telescopic tracheal tube main tube 11 achievable by compressible sections can have an extended length of at least twice a length of the same when all sections are compressed. In specific use, when the telescopic tracheal tube main tube 11 moves from the oral cavity into the trachea, the sections at a distal end of the tracheal tube are first being extended, and when the telescopic tracheal tube main tube is retrieved back from the trachea to the oral cavity, the sections at a proximal end of the tracheal tube are first being compressed. Each of the sections has a thickness of less than 1.3 mm.

Specifically, as shown in FIG. 3 to FIG. 5, in the medical supportable variable tracheal tube ventilation device provided by an embodiment of the present invention, a guiding tube 4 can be provided inside the tracheal tube main tube 11. Rail holes 41 are provided on the guiding tube 4 along an axial direction of the guiding tube 4; and elastic support members 5 are provided in the tracheal tube main tube 11 along an axial direction of the tracheal tube main tube 11; the elastic support members 5 provide circumferential support of the tracheal tube main tube 11; a diameter of each of the elastic support members 5 is preferably 0.1 mm to 0.2 mm. In actual assembly and use, the guiding tube 4 is disposed through eyelets 55 of the elastic support members 5, and the tracheal tube main body 1 can telescopically slide on the guide tube 4.

Further, in the medical supportable variable tracheal tube ventilation device provided by an embodiment of the present invention, the guiding tube 4 participates in ventilation, and the plurality of rail holes on a wall of the guiding tube 4 may have a tear drop shape and participate in ventilation.

Further, a diameter of a head portion of each of the tear drop shaped rail holes on the guiding tube 4 is 1 mm, and a diameter of a tail portion thereof is 0.1-0.2 mm. Of course, specific values of the diameters should not be limited to the values described herein. Other reasonable values should be possible, and will not be discussed one by one in detail herein.

Preferably, in actual manufacturing, the elastic support members 5 of the medical supportable variable tracheal tube ventilation device provided by an embodiment of the present invention can be springs.

In practical applications, as shown in FIG. 1 to FIG. 5, in the medical supportable variable tracheal tube ventilation device provided by an embodiment of the present invention, the tracheal tube sealing cuff 2 can be connected with an inflation valve 6 so as the inflation valve 6 inflates the tracheal tube sealing cuff 2.

The medical supportable variable tracheal tube ventilation device provided by an embodiment of the present invention can minimize tracheal tube induced irritation to the airway during perioperative general anesthesia, and effectively increases patient's tolerance, and is also safer. In addition, the patient can make a conversation when awake even with the tracheal tube, and recovery of the patient or re-insertion of the tracheal tube to the patient can be achieved at any time in case of emergency. The present invention is therefore especially suitable for a patient who needs to use the tracheal tube when being transferred back to the ward or ICU. Besides, the present invention can extend the intubated time period for patients requiring respiratory muscle support, thereby effectively reducing the possibility of incision on the trachea.

The present invention is designed based on the theoretical study of Tool Sequential Extubation (TSE) proposed by the inventors. Tool Sequential Extubation (TSE) relates to the study of a set of practical tools used during recovery from perioperative general anesthesia. Switching the tools to be used allows strong irritation to be gradually relieved as the patient gradually recovers from deep general anesthesia so as to eliminate bucking and coughing reflexes, reduce the possibility of complications, and improve the safety of anesthetized perioperative period. The medical supportable variable tracheal tube ventilation device provided by the present invention is suitable for patients of all kinds of surgeries, and it is expected that the present invention can be widely used as a common tool. The present invention is especially suitable for ICU patients and long-term intubated patients to avoid airway incision.

Figure 6:
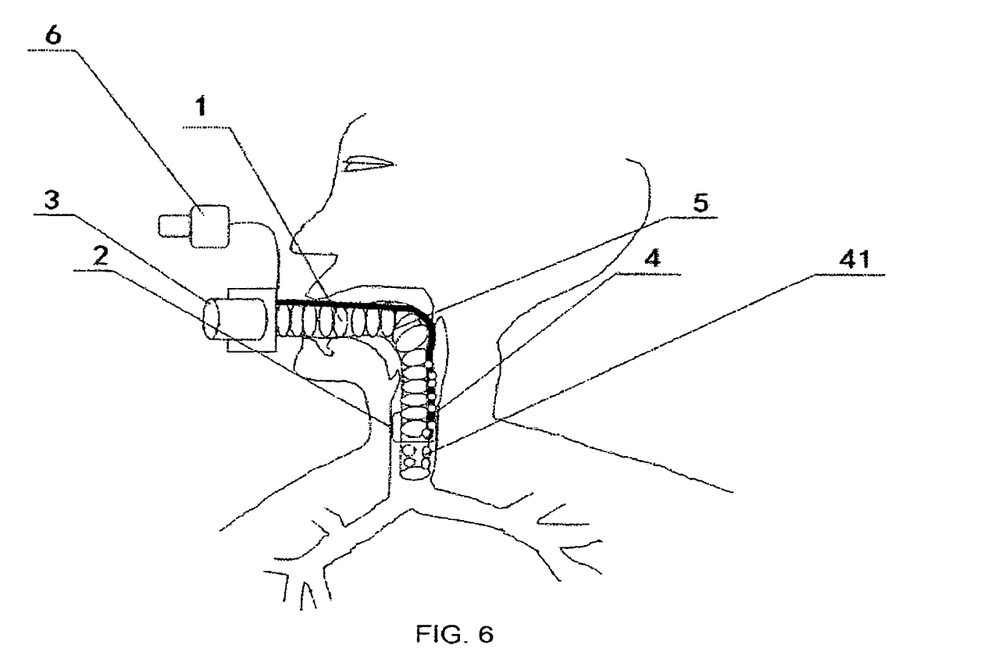
FIG. 6 is a schematic structural view of a patient using the medical supportable variable tracheal tube ventilation device provided by an embodiment of the present invention in an anesthetized and intubated condition.
Figure 7:
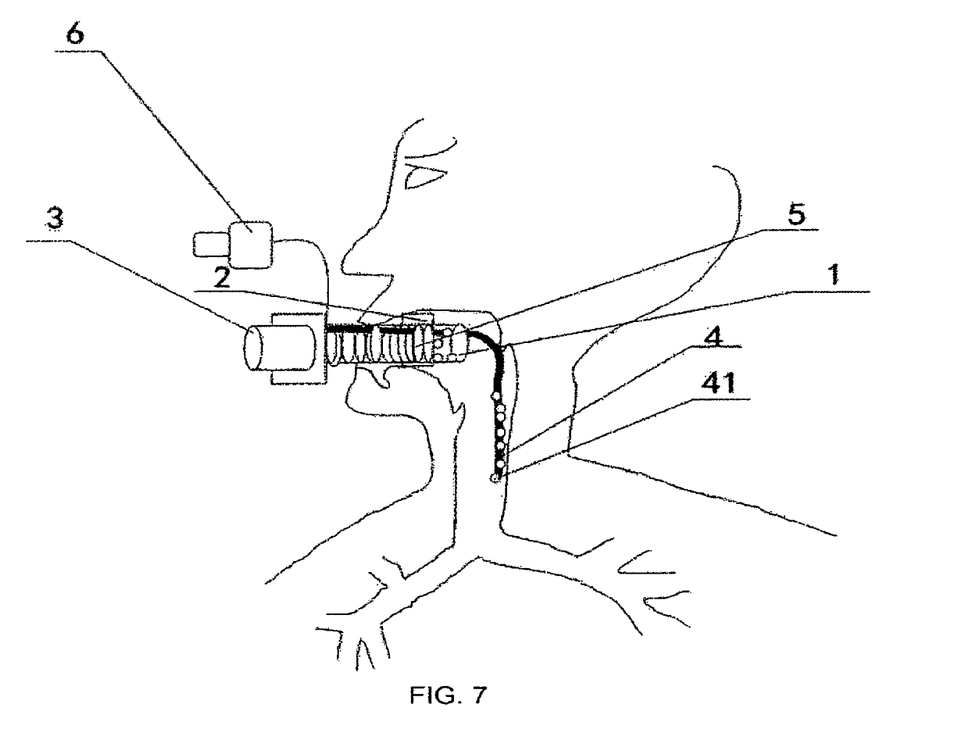
FIG. 7 is a schematic structural view of a patient using the medical supportable variable tracheal tube ventilation device provided by an embodiment of the present invention in a partially conscious condition where the tracheal tube is retrieved back to the oral cavity.
Figure 8:
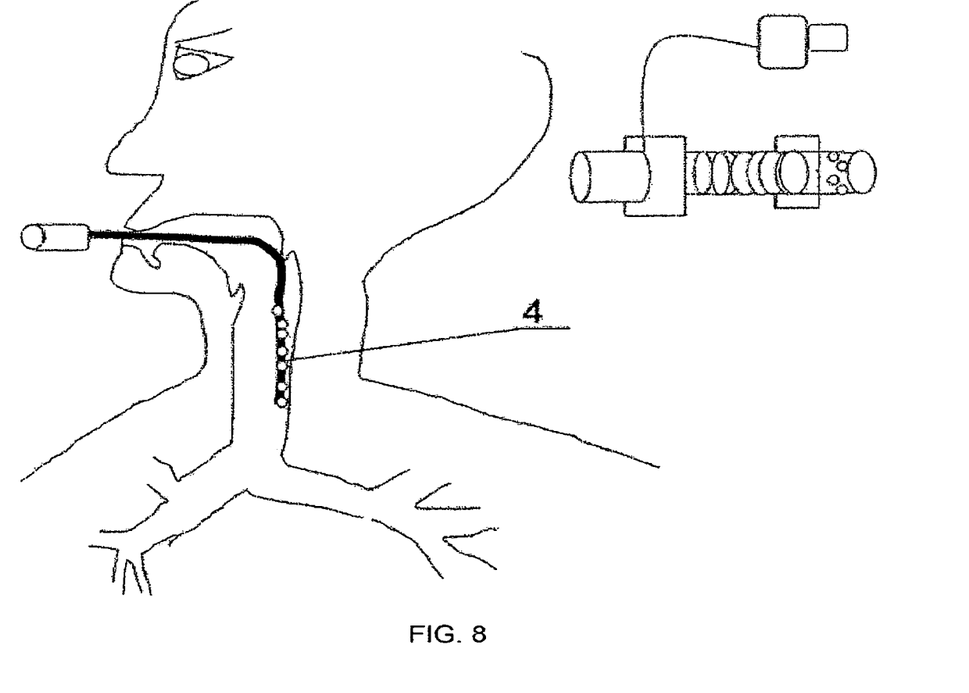
FIG. 8 is a schematic structural view of a patient using the medical supportable variable tracheal tube ventilation device provided by an embodiment of the present invention in a fully conscious condition where the tracheal tube is removed.

FIG. 6 is a schematic structural view of a patient using the medical supportable variable tracheal tube ventilation device provided by an embodiment of the present invention in an anesthetized and intubated condition; FIG. 7 is a schematic structural view of a patient using the medical supportable variable tracheal tube ventilation device provided by an embodiment of the present invention in a partially conscious condition where the tracheal tube is retrieved back to the oral cavity; FIG. 8 is a schematic structural view of a patient using the medical supportable variable tracheal tube ventilation device provided by an embodiment of the present invention in a fully conscious condition where the tracheal tube is removed.

As shown in FIGS. 6-8, during the course of clinical anesthesia when the patient is anesthetized and loses his consciousness and cannot breath spontaneously, a front end of the variable tracheal tube head 12 is in a cone shape or compressed cone shape which can reduce the damage to oral tissues and the glottis; after passing through the glottis, the tracheal tube sealing cuff 2 is inflated to prevent air leakage during supported breathing while using the anesthesia machine. The pressure on the tracheal tube wall imposed by the tracheal tube sealing cuff 2 during inflation is supported by telescopic and compressible elastic support members 5 to prevent the tracheal tube from collapsing and causing ventilation devicey dysfunction; by heating or inflating the interior of the tracheal tube, the variable tracheal tube head 12 changes from cone/compressed cone shape into cylindrical shape. After surgery when the patient resumes spontaneous breathing and is recovered from anesthesia into a relatively safe and awaken stage, the tracheal tube sealing cuff 2 is deflated, and the tracheal tube main body 1 is retrieved back to the oral cavity. Now, the patient's respiratory rate (RR) is normal, and various ventilation indexes are within relatively safe range. After the tracheal tube main body 1 is retrieved back to the oral cavity, the irritation to the trachea is relieved, and the possibility of bucking and coughing of the patient is reduced. Besides, retrieval of the tracheal tube main body 1 back to the oral cavity can maintain patency and smoothness of oral ventilation, so as to prevent obstructed ventilation due to the collapse of the oral tissues and glossoptosis. Moreover, the guiding tube 4 is retained in the trachea for air supply. The guiding tube 4 is retained in case it is necessary to timely re-intubate the tracheal tube main body 1 to the trachea to resume controlled ventilation when the patient has respiratory depression during recovery from anesthesia, thereby ensuring the safety of the patient. When the patient is fully recovered, the tracheal tube main body 1 can be pulled out to reduce the irritation to the oral cavity, and only the guiding tube 4 is retained to supply oxygen. When the patient has respiratory depression, the tracheal tube main body 1 can be inserted back to the trachea through the guiding tube 4, thus ensuring safety. For patients who are required to be intubated in ICU, the present invention can allow the tracheal tube main tube to be conveniently and safely cleaned and disinfected and thereby prolonging intubated time period and reducing the chance of airway incision. The above use of the present invention is based on the Tool Sequential Extubation (TSE) method proposed by the inventors.

The above description only describes the more preferred embodiments of the present invention, and should not be considered limiting. Any changes, replacements and modifications made within the principles and spirits of the present invention should fall within the scope of protection of the present invention.

What is claimed is:

1. A medical supportable variable tracheal tube ventilation device, comprising:
    a tracheal tube main body; which has a compressible length and comprises:
        a compressible tracheal tube main tube achieved by compressible sections; and
        a variable tracheal tube head coupled to one end of the tracheal tube main tube;
            the tracheal tube head is made of a material shapable according to different temperatures: when the temperature is above 30 degrees Celsius or 86 degrees Fahrenheit, the variable tracheal tube head opens to form a cylindrical shape; when the temperature is below 10 degrees Celsius or 50 degrees Fahrenheit, the variable tracheal tube head returns to a tapered shape;

alternatively, an interior of the tracheal tube main body is configured to be inflatable to allow the variable tracheal tube head to expand from the tapered shape to the cylindrical shape;

a tracheal tube sealing cuff sleeving an outer side of the tracheal tube main body; the tracheal tube sealing cuff is disposed proximal to the variable tracheal tube head;

a tracheal tube connector connected with another end of the tracheal tube main tube body; and a guiding tube provided inside the tracheal tube main tube; the guiding tube is provided with rail holes thereon along an axial direction thereof;

elastic support members are provided in the tracheal tube main tube along an axial direction of the tracheal tube main tube: the elastic support members provide circumferential support of the tracheal tube main tube: a diameter of each of the elastic support members is 0.1 mm to 0.2 mm; the guiding tube is disposed through eyelets of the elastic support members' the tracheal tube main body is configured to be compressible and slidable on the guide tube.

2. The medical supportable variable tracheal tube ventilation device according to claim 1, wherein when the variable tracheal tube head is in the cylindrical shape for ventilation, a diameter of the variable tracheal tube head is equal to a diameter of the tracheal tube main tube.

3. The medical supportable variable tracheal tube ventilation device according to claim 1, wherein the variable tracheal tube head is provided with side openings.

4. The medical supportable variable tracheal tube ventilation device according to claim 3, wherein a quantity of the side openings is more than two.

5. The medical supportable variable tracheal tube ventilation device according to claim 4, wherein the side openings are distributed to form a triangular shape within a three-dimensional space.

6. The medical supportable variable tracheal tube ventilation device according to claim 4, wherein the side openings are distributed in a cross shape within a three-dimensional space.

7. The medical supportable variable tracheal tube ventilation device according to claim 4, wherein the side openings are distributed in a rectangular shape within a three-dimensional space.

8. The medical supportable variable tracheal tube ventilation device according to claim 1, wherein the tracheal tube main tube is made of antibacterial PVC elastic film or antibacterial paper material elastic film;

a thickness of the PVC elastic film or paper material elastic film is from 0.07 mm to 0.17 mm.

9. The medical supportable variable tracheal tube ventilation device according to claim 8, wherein the compressible tracheal tube main tube achieved by compressible sections has an extended length of at least twice a length of the same when all sections are compressed.

10. The medical supportable variable tracheal tube ventilation device according to claim 1, wherein the guiding tube is configured to participate in ventilation, and each of the rail holes on a wall of the guiding tube has a tear drop shape and is configured to participate in ventilation.

11. The medical supportable variable tracheal tube ventilation device according to claim 10, wherein a diameter of a head portion of each of the tear drop shaped rail holes on the guiding tube is 1 mm, and a diameter of a tail portion thereof is 0.1-0.2 mm.

12. The medical supportable variable tracheal tube ventilation device according to claim 1, wherein each of the elastic support members is a spring.

13. The medical supportable variable tracheal tube ventilation device according to claim 1, wherein the tracheal tube sealing cuff is connected with an inflation valve.

* * * * *